United States Patent
Greenberger

(10) Patent No.: US 6,258,354 B1
(45) Date of Patent: Jul. 10, 2001

(54) METHOD FOR HOMING HEMATOPOIETIC STEM CELLS TO BONE MARROW STROMAL CELLS

(76) Inventor: Joel S. Greenberger, 28 Blueberry La., Lincoln, MA (US) 01773

(*) Notice: Subject to any disclaimer, the term of this patent is extended or adjusted under 35 U.S.C. 154(b) by 0 days.

(21) Appl. No.: 07/888,203

(22) Filed: May 26, 1992

Related U.S. Application Data

(63) Continuation of application No. 07/415,186, filed on Sep. 29, 1989, now abandoned.

(51) Int. Cl.[7] .......................... A01N 63/00; A01N 43/04; A61K 48/00; A61K 31/78

(52) U.S. Cl. .................. 424/93.21; 514/44; 435/455; 435/325; 435/320.1

(58) Field of Search ................................. 435/172.3, 455, 435/325, 320.1; 424/93, 93.21; 514/44

(56) References Cited

PUBLICATIONS

Pierce et al. Sulnce 239:628, 1988.*
Ankles area et al. PNAS 84: 7681, 1987.*
Ohkawa et al. Cincer Res 47:2879, 1987.*

\* cited by examiner

*Primary Examiner*—Karen M. Hauda
*Assistant Examiner*—Jill D. Martin
(74) *Attorney, Agent, or Firm*—Fish & Richardson P.C.

(57) ABSTRACT

This invention pertains to a method for homing hematopoietic stem cells to bone marrow stromal cells in a host. The method comprises, administering to the host genetically-engineered hematopoietic stem cells capable of expressing a first member of a ligand-receptor binding pair. The stem cells are administered to the host under conditions whereby binding of the first member of the ligand-receptor binding pair to the second member of the ligand-receptor binding pair, present on stromal cells, occurs thereby homing the stem cells to the stromal cells. This method is useful for transplanting bone marrow in a host or in treating a host afflicted with a disease associated with a disorder of the bone marrow.

9 Claims, 6 Drawing Sheets

TRANSFECTION AND ISOLATION OF CELL LINES
ADHERENT STROMAL CELL LINE
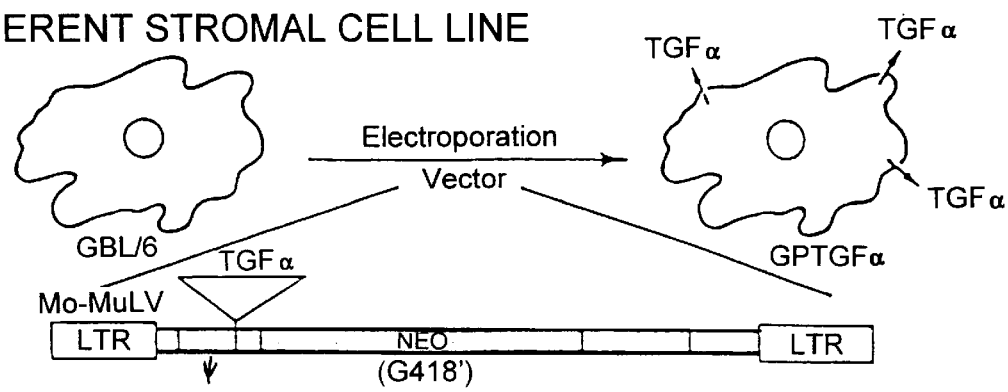
IL-3 DEPENDENT HEMATOPOIETIC CELL LINE
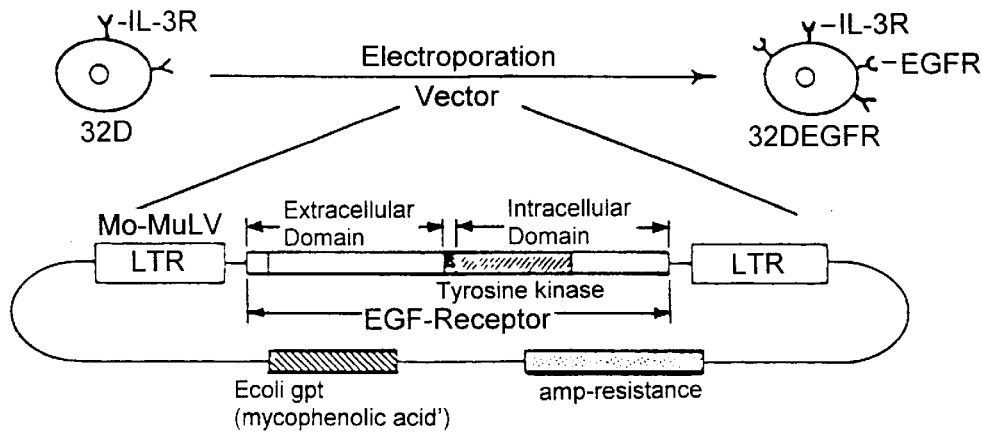
FIG. 1

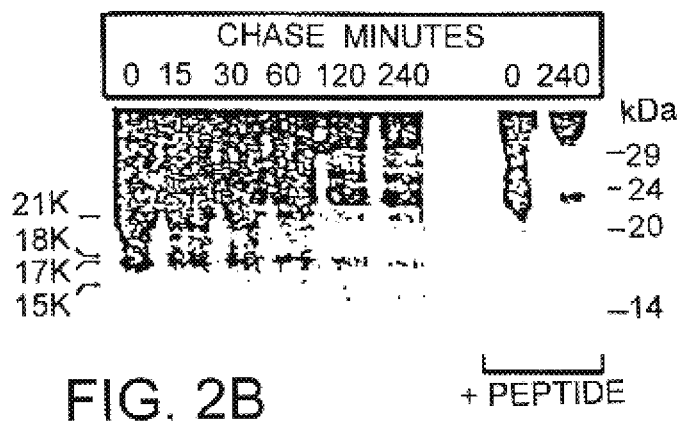
FIG. 2A
FIG. 2B
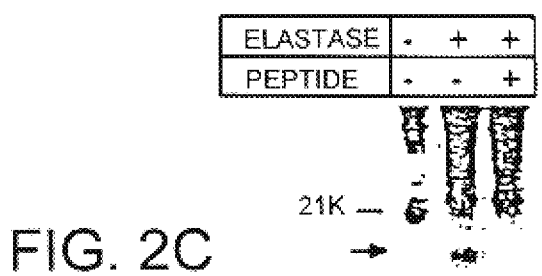
FIG. 2C
FIG. 5

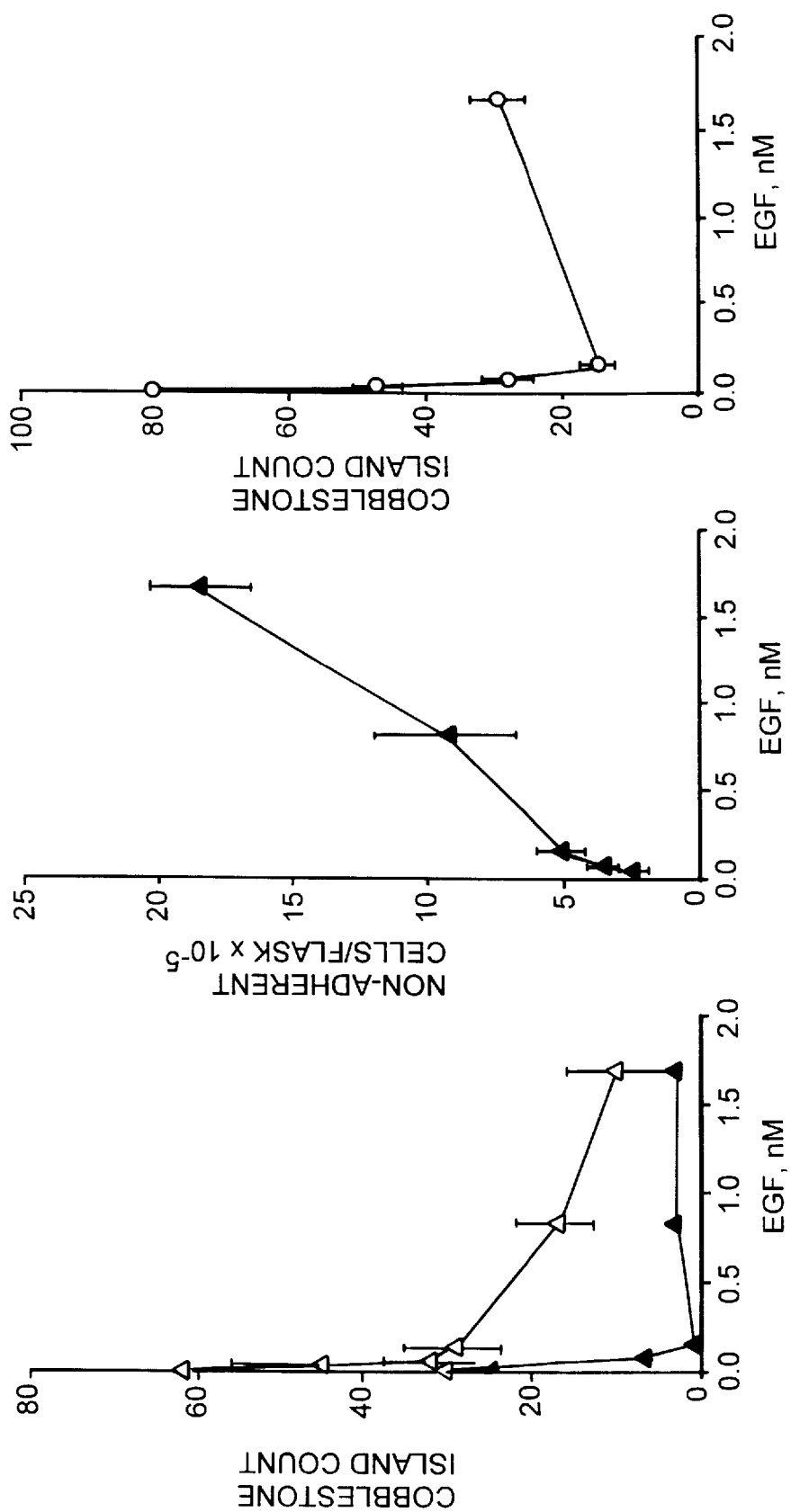

METHOD FOR HOMING HEMATOPOIETIC STEM CELLS TO BONE MARROW STROMAL CELLS

This application is a continuation of U.S. Ser. No. 07/415,186, filed Sep. 29, 1989, now abandoned, and which is incorporated herein in its entirety.

GOVERNMENT SUPPORT

Work described herein was supported by grants from the National Institutes of Health and the National Cancer Institute.

BACKGROUND OF THE INVENTION

Long-term bone marrow cultures (LTBMC) contain two major cell populations referred to as compartments. The hematopoietic stem cell compartment, contains cells at various stages of self renewal capacity and differentiation and the adherent cell or stromal cell compartment has been shown to provide the environment necessary for the production and differentiation of hematopoietic stem cells and their progenitors. Both compartments interact to facilitate hematopoiesis in vitro (Naparstek, et al; *Exp. Hematol.* 13: 701–708 (1985).

Bone marrow transplants are widely used for treating congenital disorders of the bone marrow or hematopoietic stem cell, e.g. aplastic anemia, acute leukemias, recurrent lymphomas, or solid tumors. Prior to receiving a bone marrow transplant, the recipient is prepared by ablating or removing endogenous recipient hematopoietic stem cells. This preparation is usually carried out by total body irradiation or delivery of a high dose of an alkylating agent or other chemotherapeutic cytotoxic agents (Greenberger, J. S., *Br. J. Hematol*, 62: 606–605, 1986; Anklesaria, P., et al, *PNAS, USA*, 84: 7681–7685, 1987; Thomas, E. D., *Cancer*, 49: 1963, 1982; Thomas, E. D., *N. Eng. J. Med.*, 292: 832–843, 895–902, 1975). Following preparation of the recipient, donor bone marrow cells are injected intravenously and have been demonstrated to home to multiple sites within the recipient where they proliferate and reconstitute all elements of the hematopoietic stem cell compartment including neutrophilic granulocytes, megakaryocytes (platelets), red blood cell progenitors leading to mature erythrocytes, T-lymphocytes, B-lymphocytes, monocyte/macrophages, basophils and mast cells (Thomas, E. D., cited supra). Some data from several clinical transplanation centers suggest that donor origin stromal cells of the hematopoietic microenvironment are also detected in small numbers in recipients after marrow transplant (Thomas, E. D., cited supra).

Two general categories of marrow transplanation have been described. In an allogeneic transplant, HLA tissue typing is carried out on various marrow donors and a matched marrow specimen as close as possible to that of the recipient, is used as the donor cell population. Allogeneic marrow transplant is the most common form of transplant in patients with malignancy of the marrow compartment where removal of the malignant cells from the marrow is a very difficult process (Thomas, E. D., cited supra).

The other category of bone marrow transplant is autologous marrow transplant. An autologous marrow transplant involves removal of the patient's own bone marrow and washing or preparing it by techniques that remove unwanted populations of cells (including tumor cells). The washed cells are then reinfused into the patient after the preparative regimen is completed. Under these conditions, the problems of graft versus host disease, or rejection of non-matched marrow can be reduced or eliminated. Thus, there is a decreased risk of infection or graft failure.

Autologous marrow transplant is gaining popularity and frequency throughout the United States and Europe for the treatment of solid tumors or recurrent lymphomas. For these treatments, higher doses of chemotherapy and radiation therapy can be delivered. For this technique, there must be a source of untreated marrow available to give back to the patient. Autologous marrow transplant is generally the safer form of bone marrow transplantation because it overcomes many of the immune, histocompatibility, and rejection problems. Further, an autologous marrow transplant requires less of a support facility for a new hospital or treatment center setting up such a program (Thomas, E. D., cited supra).

Graft failure is a common complication of marrow transplantation with both autologous and allogeneic protocols (Thomas, E. D., cited supra). The mechanism of graft failure has been studied for many years. Clinical research data presented at national and international meetings over the last ten years has pointed toward a defect in bone marrow stroma as the cause of graft failure. Such a defect in marrow stroma may be attributable to the preparative regimen of total body irradiation and/or chemotherapy that is used to prepare the patient for the transplant (autologous or allogeneic). In some diseases, such as chronic myelogenous leukemia, a defect in marrow stroma can be an inherent part of the disease process.

SUMMARY OF THE INVENTION

This invention pertains to a method for homing hematopoietic stem cells to bone marrow stromal cells in a host comprising, administering to the host genetically-engineered hematopoietic stem cells capable of expressing a first member of a ligand-receptor binding pair. The stem cells are administered to the host under conditions whereby binding of the first member of the ligand-receptor binding pair to the second member of the ligand-receptor binding pair, present on stromal cells, occurs thereby homing the stem cells to the stromal cells.

Another embodiment of the method for homing hematodoietic stem cells to bone marrow stromal cells in a host can comprise a first step of administering to the host stromal cells capable of expressing a first member of a ligand-receptor binding pair followed by a second step of administering hematopoietic stem cells capable of expressing a second member of a ligand-receptor binding pair. In this embodiment, either the stem cells or stromal cells or both the stem cell and stromal cell are genetically-engineered to provide the capability of expressing the appropriate ligand or receptor. The methods of this invention can be used for transplanting bone marrow in a host or for treating a host afflicted with a disease associated with a disorder of the bone marrow.

Transplantation of a donor bone marrow microenvironment, including both the stromal and stem cells, can reduce the risk of graft failure in instances where a defect in a patient's stroma is causing the graft failure. A problem encountered when attempting to transplant two cell lines which are dependent on each other is that there are multiple possible sites in a host where the cells can "home". Thus, there is a chance that the cell lines may not "home" together. The method of this invention provides a method for homing stem cells to the engrafted microenvironment thereby allowing proliferation of the stem cells at these new sites to produce all the formed elements of the blood. The method of homing stem cells to stromal cells is advantageous in that it can be used to reconstitute the marrow of patients who have damaged marrow stroma and stem cells due to injury, congenital defects, or cytotoxic therapy,

DESCRIPTION OF THE DRAWINGS

FIG. 1 is a schematic showing the transfection of a stromal cell line with an expression vector containing the Mo-MuLV LTR, the entire coding region (595 bp) for the mature 50 amino-acid transforming growth factor α (TGFα), and the neomycin gene which confers G418 resistance to mammalian cells. The transfection of a hematopoietic cell line with an expression vector containing cDNA for epidermal growth factor receptor (EGF-R), the Mo-MuLV LTR, and the E. coli GPT gene which confers resistance to mycophenolic acid is also depicted in the schematic.

FIGS. 2A–2C is a photograph of a Northern blot analysis of total mRNA from the GPTGFα (GPTα), GB1neo$^r$ and EuT cell lines, for detectable transcripts for TGFα. EuT cells were used as the positive controls. Total mRNA (10 μgs/lane) was run on a 1% agarose gel in 1% formaldehyde and transferred to a nylon membrane. Filters were hybridized with a $^{32}$P labelled specific cDNA (542 bp insert), washed at high stringency and autoradiograms exposed for three to four days at −70° C. with intensifying screens. A 4.8 Kb specific message indicating the presence of proTGF-α mRNA was detected in the GPTGFα cells while no detectable expression of the TGF-α gene was detected in GB1 neo$^r$ cells. FIG. 2B is a fluorograph showing the results of pulsechase experiments evaluating the biosynthetic processing of proTGF-α in GP-TGF-α cells. Sizes of marker proteins are at right, and those of pro-TGF-α (21 kDa) and its products are at left. FIG. 2C is a fluorograph of $^{35}$S-cysteine labelled GP-TGF-α cells exposed to elastase or medium alone and immunoprecipitated with anti-pro-TGF-α antibody alone or with excess immunogenic synthetic peptide.

FIG. 3A shows the cumulative number of "cobblestone areas" per flask for over fifty days in culture. FIG. 3B shows the cumulative production of non-adherent cells/flask for over fifty days in culture. Factor-dependent 32D-EGF-R cells plated without interleukin-3 (IL-3) or epidermal growth factor (EGF) or stromal cells were not viable at four days in culture and did not adhere to plastic. There was a strong and clear effect that GPTGFα cells support 32D-EGFR cells in vitro in the adherent population and growth after detachment.

FIG. 5 is a scan of $^{111}$In-32D or $^{111}$In-fresh bone marrow (FBM) cells in vivo, Factor dependent-32D cells or fresh bone marrow cells were labelled for twenty minutes with In-Oxine (300 μCi/$10^7$ cells). The labelled cells were injected intravenously into lethally irradiated (1000 cGy) C57BL/6 mice. The mice were anaeschetized twenty-four hours posttransplant by using an inhalation anesthetic, methoxyflurane. Subsequently, the mice were scanned using a gamma camera (Picker) connected to a PDP-11 digital computer for twenty minutes. The arrows indicate localization of labelled cells (FBM) but not 32D cells to the high dose irradiated right hind limb as well as the liver and spleen (central dark area).

FIGS. 7A–C is a set of graphs depicting the inhibition of 32D-EGFR cell adhesion by soluble EGF receptor ligands.

DETAILED DESCRIPTION

Figure 3A:
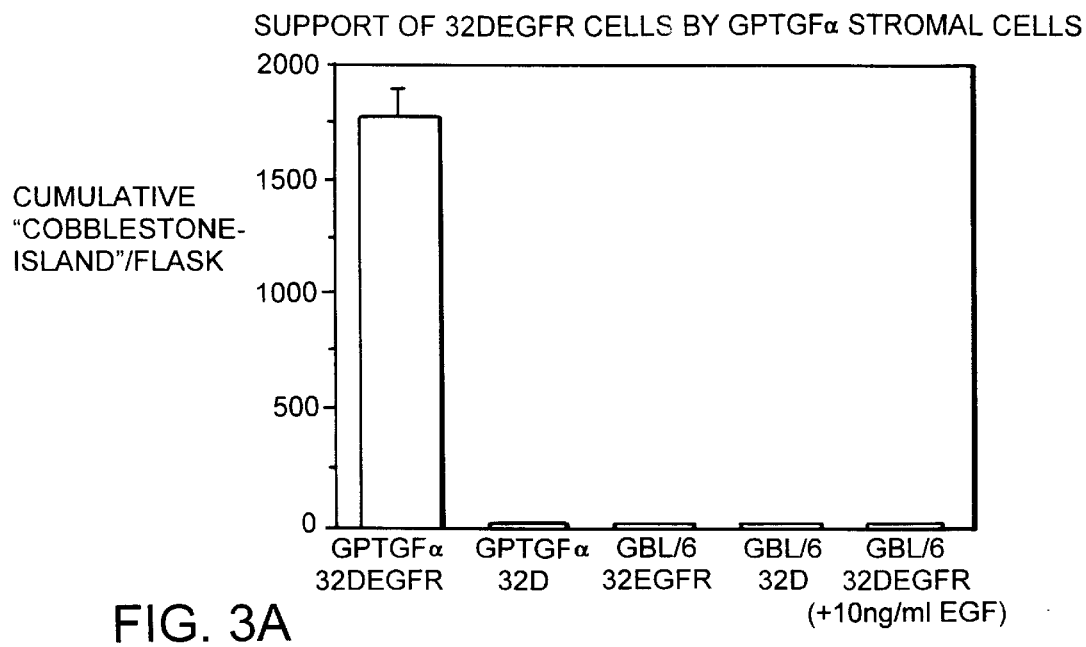
FIGS. 3A and 3B are graphs depicting the support of 32D-EGFR cells by a TGFα producing GPTGFα stromal cell line. The 32D-EGF-R cells ($2.5 \times 10^6$) were cocultivated with confluent cultures of GBL/6 or GPTGFα cells. At weekly intervals, "cobblestone areas" were scored and non-adherent cells were harvested and counted. The flasks were refed by adding an equal volume of fresh medium. The results are expressed as the mean ±SD of three flasks per experiment.

This invention pertains to a method for homing hematopoietic stem cells to bone marrow stromal cells in a host. The method comprises administering to the host genetically engineered hematopoietic stem cells capable of expressing the first member of a ligand receptor binding pair under conditions whereby binding of the first member of the ligand receptor binding pair to a second member of the ligand receptor binding pair, present on stromal cells, occurs thereby homing the stem cells to the stromal cells.

When it is desired to replace the stroma in a host, the method comprises a step of administering to the host stromal cells capable of expressing a first member of a ligand receptor binding pair followed by hematopoietic stem cells capable of expressing a second member of a ligand receptor binding pair. The cells are administered under conditions whereby binding of the ligand to the receptor occurs thereby homing the stem cells to the stromal cells.

In this embodiment, either the stem cells or the stromal cells or both the stem cells and the stromal cells are genetically-engineered to provide the capability of expressing the appropriate ligand or receptor. When the methods are used to treat a host afflicted with a bone marrow associated disease, a therapeutically effective amount of stromal cells capable of expressing a first member of a ligand receptor binding pair and a therapeutically effective amount of hematopoietic stem cells capable of expressing a second member of the ligand receptor binding pair are administered to the host.

Hosts which can be used within this invention are animals susceptible to bone marrow disorders or which may need a bone marrow transplant (i.e., animals which have bone marrow). Examples of hosts include humans and domestic animals (e.g., dogs, cats, and horses).

The hematopoietic stem cells and bone marrow stromal cells are preferably derived from the species of host being treated or can be derived from a species which does not invoke significant immune responses in the host. The stem cells or stromal cells can also be derived from the host if the cells are functioning properly. The stromal and/or stem cells can be removed from the host and cultured using conventional techniques. Examples of human haematpoietic stem cell lines which can be used in this invention include nonadherent cells derived from human long-term bone marrow cultures. See Greenberg, H. M., et al, *Blood*, 1981, Vol. 58, Dp 724–732, the contents of which are hereby incorporated by reference. Examples of human bone marrow stromal cells include KM101, KM102, KM103, KM104 and KM105. See Fitzgerald et al, *Int. J. Radiation Oncoloyy Biol. Phys.* Vol 15, pp 1153–59 (1988), the contents of which are hereby incorporated by reference.

The hematopoietic stem cells or stromal cells can be genetically-engineered using conventional techniques. The DNA encoding the desired ligand or receptor can be inserted into a vector and introduced into the cells using techniques such as electroporation and/or retroviral infection. Other techniques which can be used to introduce DNA into the cells are calcium phosphate precipitation (Graham and van der Eb, *Virology* 52:456 (1973) and DEAE-dextran (Cullen et al., *Nature* 307:241 (1984)).

The ligand-receptor binding pair are substances having an affinity for each other. At least one member of the ligand-receptor pair is proteinaceous. Examples of ligand-receptor binding pairs include transforming growth factor (TGF) and transforming growth factor receptor (TGFR) or EGF Receptor; (EGFR) epidermal growth factor (EGF) and EGFR; tumor necrosis factor-$\alpha$ (TNF-$\alpha$) and tumor necrosis factor-receptor (TNFR); interferon and interferon receptor; platelet derived growth factor (PDGF) and PDGF receptor; transferrin and transferrin receptor; avidin and biotin or antibiotin; antibody and antigen pairs; interleukin and interleukin receptor (including types 3, 4 and 5); granulocyte-macrophage colony stimulating factor (GMCSF) and G,4CSF receptor; macrophage colony stimulating factor (MCSF) and MCSF receptor; and granulocyte colony stimulating factor (G-CSF) and C-CSF receptor. Further, the ligand-binding pair can be a pair wherein the first member is naturallyoccurring and the second member is provided using genetic-engineering techniques. For example, the stromal cells can be genetically-engineered by inserting DNA encoding sugar receptors and this will enhance the homing of the stem cells to the stromal cells based upon the naturally-occurring sugar molecules present in stem cells (Aizawa et al; *Exp. Hematol.* 16: 811–813 (1988).

The terms ligand and receptor are intended to encompass the entire ligand or receptor or portions thereof. Portions which can be used within this invention are those portions sufficient for binding to occur between the ligand and the receptor.

The cells can be administered by subcutaneous or other injection or intravenously. In methods for treating a host afflicted with a bone marrow associated disease, a therapeutically effective amount of stem cells or stromal cells is that amount sufficient to significantly reduce or eliminate the symptoms or effects of a bone marrow associated disease. The therapeutically effective amount administered to a host will be determined on an individual basis and will be based, at least in part, on consideration of the individual's size, the severity of symptoms to be treated, and the results sought. Thus, a therapeutic effective amount can be determined by one of ordinary skill in the art of employing such practice in using no more than routine experimentation.

This invention will be further illustrated by the following example.

EXAMPLE 1

Generation of a Bone Marrow Stromal Cell Line and Purified Hematopoietic Stem Cells Human bone marrow stromal cell lines can be established using the technique described by Fitzgerald et al (1988) cited supra and Harigaya et al, *PNAS USA* 83: 3477–3488 (1985). Human stem cells can be purified from long-term bone marrow cultures using the techniques described in Greenberg, H. M., et al, *Blood*, 1981, Vol. 58, pp 724–732, the contents of which are hereby incorporated by reference.

Transfection and Isolation of Cell Lines

The vectors, pZipTGF$\alpha$ and pZipSV(x), were constructed as previously described (Finzi et al., *PNAS USA*, 84: 3733–37, (1987); William et al, Nature, 310: 476–78 (1984). Murine GB1/6 stromal cells were transfected with pZipTGF-$\alpha$ using electroporation as described by Pierce et al. (*Science*, 239: 628–31 (1988)). After twenty-four hours, the medium was replaced and the cells were selected for pZipTGF$\alpha$ transfectants in 1 mg/ml C418 (Gieneticin GIBCO). Cells which were resistant to G418 were expanded and assayed for TGF-$\alpha$ production. The cells containing the DNA encoding TGF-$\alpha$ were labeled GP-TGF-$\alpha$. A control cell population was generated by replication retroviral vector infection of the murine GB1/6 cell line using 24-hour culture supernatants from $4_2$ cells transfected with the PZip/neo DNA. This control cell population was labeled GB1neo$^r$.

Transfected and infected cells were selected for resistance to G418 (1 mg/ml) and expanded. All cells were grown in Dulbecco's modified Eagle's medium supplemented with 10% fetal bovine serum and 10 $\mu$M hydrocortisone sodium succinate. The generation of ZipTGF cells by infection of NIH-3T3 mouse fibroblasts with pZip-TGF$\alpha$ has been described (Finzi et al, cited supra; DiMarco et al, *Oncogene* 4, 831–838 (1989)). ZipTGF clone EUT was used in the present examples.

Transfection and selection of IL-3-dependent murine 32D stem cells with a retroviral vector construct containing the human EGF receptor cDNA has been described (Pierce et al, *Science* 239, 628–631 1988). 32D-EGFR cells respond to EGF at concentrations ranging from 0.15 nM to 5nM. 32D-EGFR cells and parental 32D cells were maintained as suspension cultures in RPMI 1640 medium supplemented with 10% fetal calf serum and EGF (Pierce et al, cited supra) or IL-3 (Greenberger et al, Fed. Proc. 42, 106–115 1983; Ohta et al, Pathol. *Immunopathol. Res.* 8, 1–20 1989) as previously described.

Generation of a Stromal Cell Line that Expresses pro TGF-$\alpha$ on the Cell Surface The murine b-one marrow stromal cell line, GB1/6, supports myelropoiesis of enriched progenitors from long-term bone marrow cultures, but does not support adhesion or proliferation of the interleukin-3 (IL-3)-dependent hematopoietic progenitor cell line, 32D (Anklesaria et al, *Proc. Natl. Acad. Sci. USA* 84, 7681–7685 1987); Greenberger et al, cited supra). GB1/6 cells were transfected with the retrovirus expression vector pZip-TGF$\alpha$ containing the entire coding region for human proTGF-$\alpha$ transcribed under the control of a retroviral LTR (Finzi et al, cited supra (1987)) to obtain a GB1/6 derivative that would express pro-TGF-$\alpha$. The same vector lacking the proTGF-$\alpha$ cDNA insert, pZIP/neo, was introduced into GB1/6 to generate a control cell population. The resulting cells expressing these vectors were designated GP-TGF-$\alpha$ and GB1neo$^r$, respectively, and were selected for resistance to C418 conferred by expression of the bacterial transposon Tn5 neomycin resistance gene (Cepko et al, *Cell* 37:1653–62 (1984)) present in the vectors. Both cell mass populations were expanded and analyzed for their ability to express proTGF-$\alpha$. Northern blot analysis demonstrated the presence of proTCF-$\alpha$ mRNA with the expected 4.8 kb size in GP-TGF-α cells, and no detectable expression of the endogenous TGF-α gene in GB1neo$^r$ cells (FIG. 2A).

The Northern Blot Analysis was conducted as follows. PolyA+RNA was isolated from samples of at least $10^8$ cells by lysis in the presence of proteinase K and sodium dodecyl sulfate as previously described (Badley et al, *Biofeedback* 6:114–116 (1988)). Samples of polyA+RNA were electrophoresed in a 1% agarose gel, blotted onto a nylon membrane and probed with a human TGF-α cDNA radiolabeled by random-priming, as previously described (Finzi et al, cited supra (1987)).

The biosynthetic processing of proTGF-α in GP-TGF-α cells was evaluated by pulse chase metabolic labeling experiments. Cells were labeled with $^{35}$S-cysteine for fifteen minutes followed by incubation with unlabeled regular medium for various time lengths. Lysates obtained from these cells were immunoprecipitated with antibodies raised against a synthetic peptide that corresponds to a C-terminal cytoplasmic sequence of proTGF-α (Teixido et al, *Nature* 326, 883–885 1987). Polyacrylamide gel electrophoresis and fluorography of these precipitates displayed a proTGF-α biosynthesis pattern very similar to that observed in other cell lines that express proTCF-α (Bringman et al, 1987; Gentry et al, 1987, Wong et al, *Cell* 56, 495–506 1989). Thus, proTGF-α appeared as two products of 17 kd and 21 kd Immediately after the labeling pulse. These two products disappeared after fifteen minutes of metabolic chase concomitantly with the appearance of a 18 kd labeled product (FIG. 2B). Based on previous characterization of similar products from other cell lines that express proTGF-α, these products were identified as nascent proTGF-α (17 kd), fully glycosylated post-Golgi proTGF-α (21 kd), and proTGF-α cleaved at the N-terminal domain that precedes the TGF-α sequence in the precursor (18 kd).

The level of expression of proTGF-α in GP-TGF-α cells was too low to allow detection of this molecule on the cell surface by labeling with $^{125}$I and immunoprecipitation. To determine whether proTGF-α became exposed on the surface of GP-TGF-α cells, susceptibility to cleavage by elastase was tested. Elastase cleaves at the N-terminus of the TGF-α sequence (Ignotz et al, *Proc. Natl. Acad. Sci. USA* 83, 6307–6311 1986). Thus, GP-TGF-α cell monolayers radioactively labeled under conditions that preferentially label the 21 kd proTCF-α species were exposed to elastase for one hour at 4° C. This treatment resulted in quantitative conversion of the 21 kd labeled proTGF-α species to a 18 kd labeled product (FIG. 2C). This effect of elastase was dependent on the time of incubation and was not observed in control cultures that received elastase immediately before the incubation was stopped and the samples were prepared for immunoprecipitation.

These results indicated that proTGF-α synthesized in GP-TGF-α cells became rapidly exposed on the cell surface and cleaved at the N-terminus. Further processing of the molecule was a very slow process. Consistent with these results, the concentration of free TGF-α in medium conditioned for twenty four yours by GP-TGF-α was very low, below the detection limit (20pM) of our radioreceptor assay (Wong et al., *Cell* 56:495–506 (1989)) and radioimmunoassay (Ignotz et al, 1986, cited supra). By comparison, ZipTGF (clone EUT) cells that derive from NIH-3T3 cells by transfection with pZip-TGFα and express a high level of proTGF-α mRNA (Finzi et al, 1987, cited supra; and FIG. 1A) accumulated 15 nM TCF-α in the medium in twenty-four hours.

Pulse Labeling and Immunoprecipitations

For pulse labeling studies, subconfluent GP-TGF-α and GB1neo$^r$ cell monolayers were pulse labeled. for 20 minutes with 300 µCi/ml of $^{35}$S-cysteine (DuPont-New England Nuclear) in cysteine-free and serum-free Modified Eagle's Medium (MEM). The pulse label was chased by addition of complete HEM. At the indicated times, cells were rinsed once and scraped into immunoprecipitation buffer consisting of 130 mM NaCl, 20 mM sodium phosphate, 1 mM EDTA, 1 mM PMSF and 200 KIU/mi of aprotinin, pH 7. Cell pellets collected by centrifugation were then lysed in the same buffer containing 1% Nonidet P-40. In preparation for immunoprecipitation, cell lysates clarified by centrifugation at 12,000×g for ten minutes were reduced and alkylated by incubation for 20 minutes at 22°C. with 5 mM dithiothreitol and 0.25% sodium dodecyl sulfate (SDS), followed by addition of 10 mM N-ethylmaleimide and incubation for 10 minutes at 22° C. Anti-pro TGF-α IgG fraction was then added at a ½s dilution relative to the original antiserum, and the mixture was incubated overnight at 4° C. To assess specificity of the immunoprecipitated products, C-terminal proTGF-α synthetic peptides against which the antibodies had been raised (Teixido et al, 1987, cited supra). were added at a final concentration of 5 mM to the immunoprecipitation reactions. Immunocomplexes were harvested with protein A-Sepharose and washed three times with phosphate buffered saline (PBS) containing 0.1% Triton and 0.025% SDS, and once with PBS alone. The washed beads were heated in electrophoresis sample buffer for 5 min at 100° C., and were electrophoresed on 12% to 18% gradient polyacrylamidedodecyl sulfate gels followed by fluorography using Enlightning (DuPont-New England Nuclear).

For elastase treatment, GP-TGFα cells labeled with 300 µCi/ml of $^{35}$S-cysteine for twenty minutes and chased for five minutes with complete medium at 37° were chilled on ice. Cell monolayers were washed with ice-cold MEM and incubated for 1 hour at 4° C. with MEY, with or without 250 µg/ml of porcine pancreatic elastase (Worthington) and 250 µg/ml of soybean trypsin inhibitor (Sigma) to prevent proteolysis by trypsin that might contaminate the elastase preparation. Control cultures received elastase immediately before stopping the incubation. Incubations were stopped by washing the cell monolayers three times with immunoprecipitation buffer. Samples were then immunoprecipitated with ani-pro TGF-α antibodies as described above.

ECF Radioreceptor Assay

Radioreceptor assays to measure soluble TGF-α in samples of conditioned medium were performed using low density cultures of A431 cells in 2 cm$^2$ wells and $^{125}$I-EGF as the tracer radioligand. Purified EGF and TGF-α were used as standards. Experimental samples and standards were subjected to the assay either directly or after 20-fold concentration by dialysis against 0.1M acetic acid, lyophilization and resuspension in assay medium. At the end of the assays, cells were solubilized with a 1% Triton X-100 solution and counted for $^{125}$I radioactivity. Other assay conditions were as previously described (Wong et al. 989, cited supra).

Homing of A Genetically-Engineered Hematopoietic Cell Line Expressiny the EGF Receptor to Stromal Cells Expressing proTGFα

Figure 6:
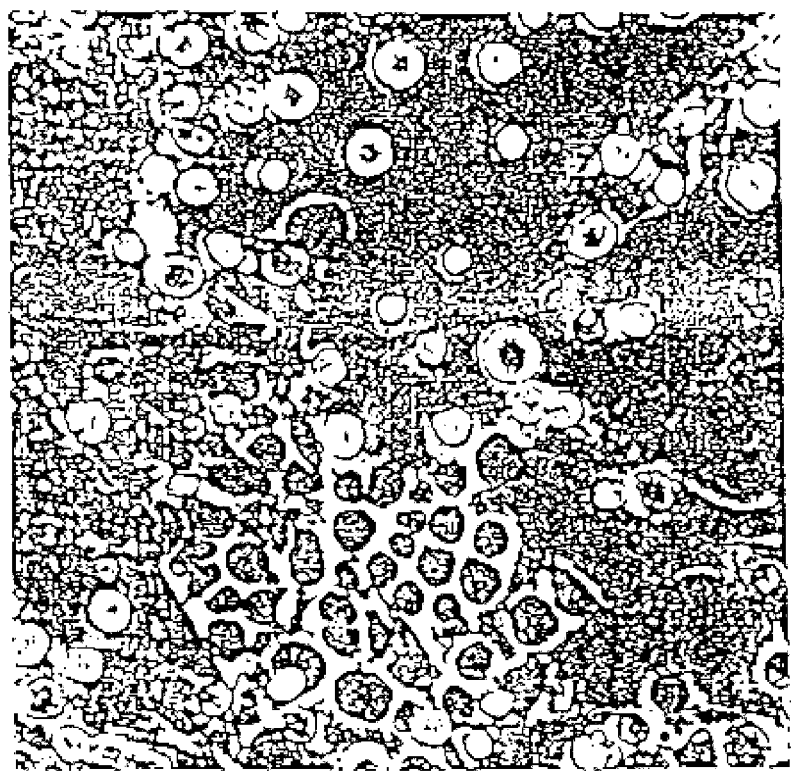
FIG. 6 is a photograph of 32D-EGFR cells forming foci of flattened adherent cells.

The hematopoietic progenitor murine cell line 32D is dependent on IL-3 for proliferation and survival, and does not respond to other hematopoietic growth factors including GM-CSF and CSF-1 (Greenberger et al, cited supra; Ohta et al, cited supra). This cell line lacks EGF receptors but expresses all the components of the intracellular pathway needed to mediate a mitogenic response to this factor, as demonstrated with the EGF receptor-transfected 32D cell clone 32D-EGFR (Pierce et al, *Science* 239: 628–631 1988). For these reasons, the 32D-EDFR cell line was chosen to test whether the EGF receptor/proTGF-α pair could mediate cell-cell adhesion and lead to a mitogenic response. 32D-EGFR cells were cocultivated with confluent monolayers of GP-TGF-α stromal cells in the absence of any added IL-3 or EGF. Within four to six days, the 32D-EGFR cells began to form foci of flattened adherent cells with approximately 10 cells/focus (FIG. 6). The morphology of these foci was typical of the "cobblestone islands" generated by primary cultures of bone marrow haematpoietic progenitors and stromal cells (Dexter et al, *J. Cell. Physiol.* 91, 335–344 1977; Williams et al, *J. Cell. Physiol.* 102, 287–295 1977; Greenberger, cited supra; Anklesaria et al, cited supra). The 32D-EGFR cell islands progressively increased in size (>25 cells/island) and number between days 6 and 40 of cocultivation (FIG. 3A, a bars). Cell Adhesion and island formation were not detected when 32D-EGFR cells were cocultivated with GB1neo$^r$ cells, or when 32D cells were cocultivated with GP-TGF-α cells or GB1neo$^r$ cells (FIG. 3A, bars b, c and d).

Figure 3B:
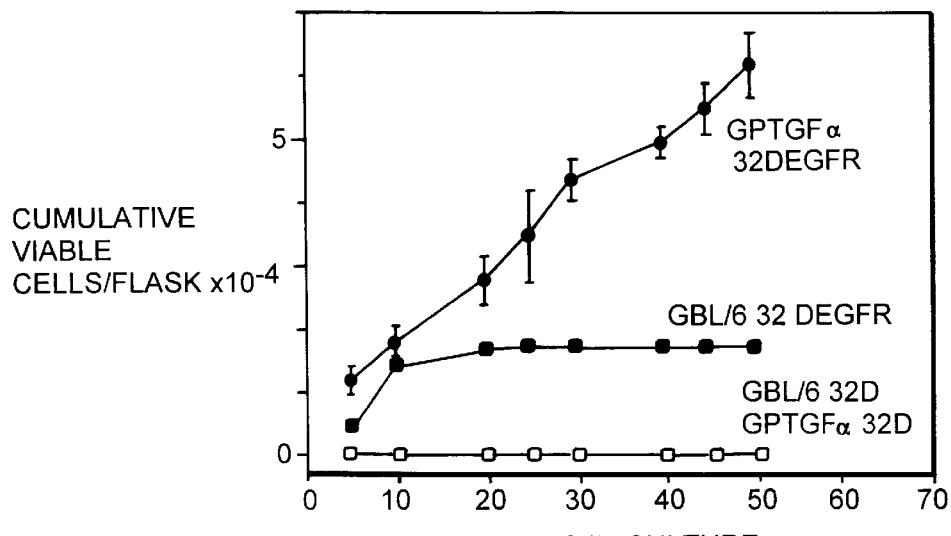
Figure 4:
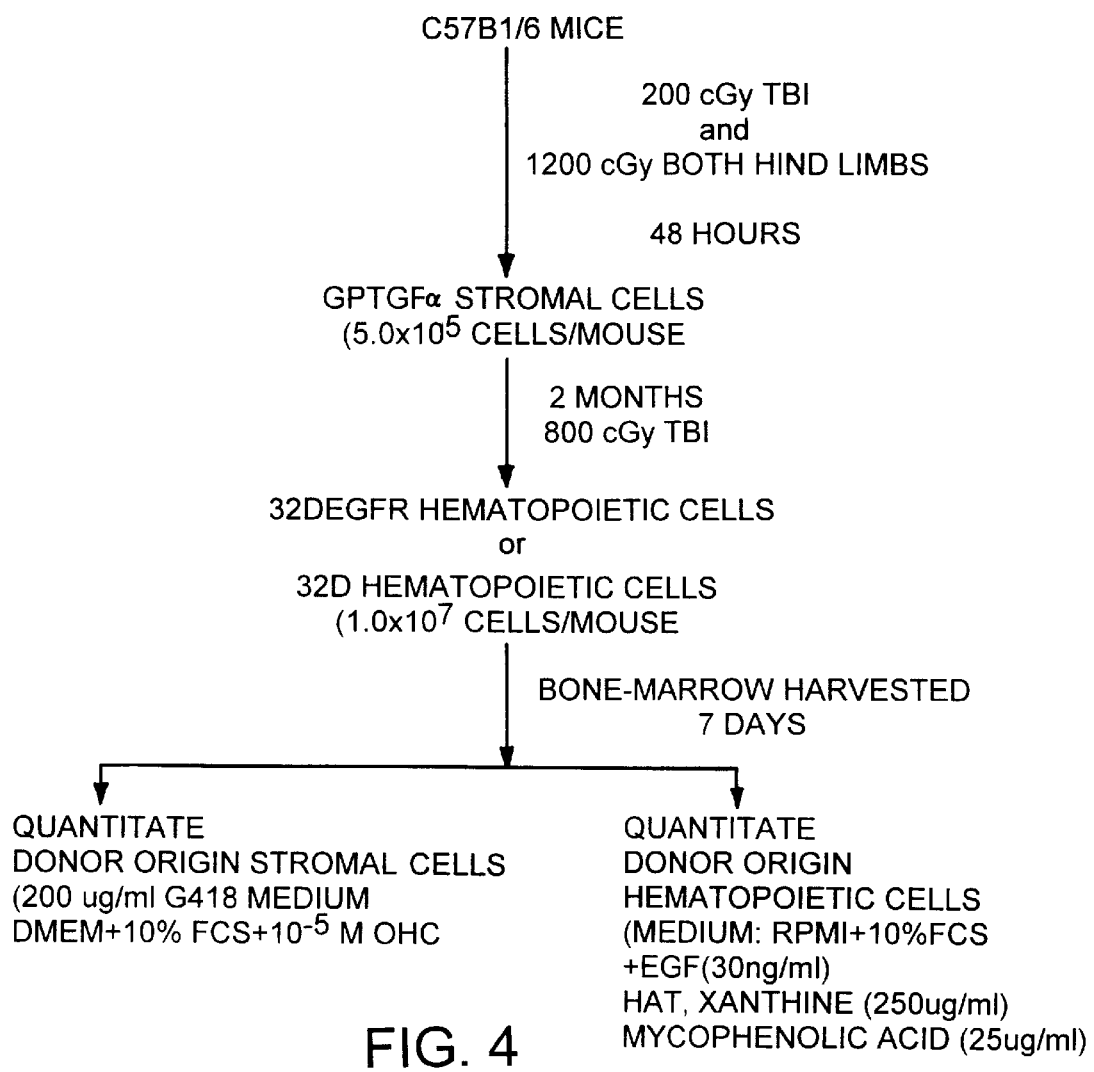
FIG. 4 is a schematic depicting the transplantation protocol. Adult mice received 3.0 Gy (TBI) and in addition irradiation to both hind limbs of 10.0–12.5 Gy, delivered by a 6 MeV Siemans linear accelerator. During irradiation mice were restrained in a lucite holder designed to shield non-boosted areas. The dose rate at several irradiated sites was measured by thermoluminescent dosimeters. The dose rate for the TBI ranged from 0.25–1.0 Gy/minute and to the exposed limb from 1.0–1.15 Gy/min.

In addition to attachment to the stromal layer, the adherent foci of 32D-EGFR cells were able to continuously release viable hematopoietic cells into the culture medium for at least forty days in culture (FIG. 3B, a bars). Cells released into culture medium had the phenotype of normal 32D-EGFR cells (Pierce et al, 1988, cited supra) as determined by their ability to respond to both EGF and IL-3, and to form colonies in semisolid medium (data not shown). In contrast, there were no viable cells (FIG. 3B, bars b and d) or less than 1% of the initial innoculum (FIG. 3B, c bars) produced when hematopoietic-stromal cells were cocultivated in combinations other than 32D-EGFR/GP-TGF-α. Hematopoietic cells plated alone in serum-supplement Medium without IL-3 or EGF lost viability within forty-eight to seventy-two hours. Other control flasks containing monolayers of stromal cells alone had fewer than 0.1% of the cells in the culture supernatant.

Adhesion to Stroma Is Mediated By EGF Receptor Binding To Membrane proTGF-α.

The specificity of "homing" and adherence of 32D-EGFR cells to GP-TGF-α monolayers was evaluated by testing the ability of EGF and TGF-α to inhibit 32D-EGFR cell binding to the monolayers. Addition of 0.04–1.7 nM EGF from the first day of cocultivation prevented the formation of 32D-EGFR cell islands in a dose-dependent manner for at least seven days (FIG. 7A). The non-adherent 32D-EGFR cells in the culture medium proliferated in the presence of added EGF (FIG. 7B). The number of viable cells harvested per flask increased with increasing concentration of added EGF. The effect of exogenous TGF-α on cocultures of 32D-EGFR cells and GP-TGF-α cells was similar to the effect of EGF. There were no detectable adherent cell islands by day nine in cocultures supplemented with 12 nM TGF-α.

The ability of exogenous EGF to induce the disappearance of preformed 32D-EGFR cell islands was also evaluated. EGF was added to seven day old cocultures of 32D-EGFR and GP-TGF-α cells that contained multiple islands. EGF had markedly decreased the number of islands within forty-eight hours after addition (FIG. 7C).

In other experiments, anti-EGF receptor serum or preimmune serum were added daily to 32D-EGFR/GP-TFG-α cocultures from the first day of cocultivation. Cocultures containing preimmune serum generated islands and sustained proliferation of 32D-EGFR cells whereas no adherent islands were detectable and only 3% of the hematopoietic cells were viable in seven day old cocultures containing anti-EGF receptor antibodies (Table 1).

TABLE 1

Effect of anti-EGF receptor antiserum on the adhesion of 32D-EGFR cells

| Serum added | Islands/dish | Viable cells/dish |
| --- | --- | --- |
| Preimmune | 69 | 1.42 × 10$^5$ |
| Anti-EGFR | 0 | 0.05 × 10$^5$ |

Confluent monolayers of GP-TGF-α cells in 35 mm dishes were cocultured with 2×10 32D-EGFR cells per dish. Rabbit preimmune serum or anti-EGF receptor serum was added daily to these cocultures at 1:1000 dilution. The number of adherent cell islands/dish and viable non-adherent cells/dish was scored on day 7 after initiation of the cocultures. Results are the mean of triplicate dishes.

Proliferation of Hematopoietic Cells In Contact With Stroma

The sustained increase in 32D-EGFR cell number observed in cocultures with GP-TGF-α cells could be due to proliferation of non-adherent cells released from the adherent islands. Although the level of soluble TGF-α in the conditioned medium of GP-TGF-α cells was below the 20 pM detection limit of our assays, generation of a small amount of TGF-α by cleavage of membrane proTGF-α might be sufficient to stimulate non-adherent cells located near the GP-TGF-α cell monolayer. Alternatively, mitogenic stimulation of 32D-EGFR cells could occur while they were anchored to the monolayers via membrane proTGF-α.

Figure 8:
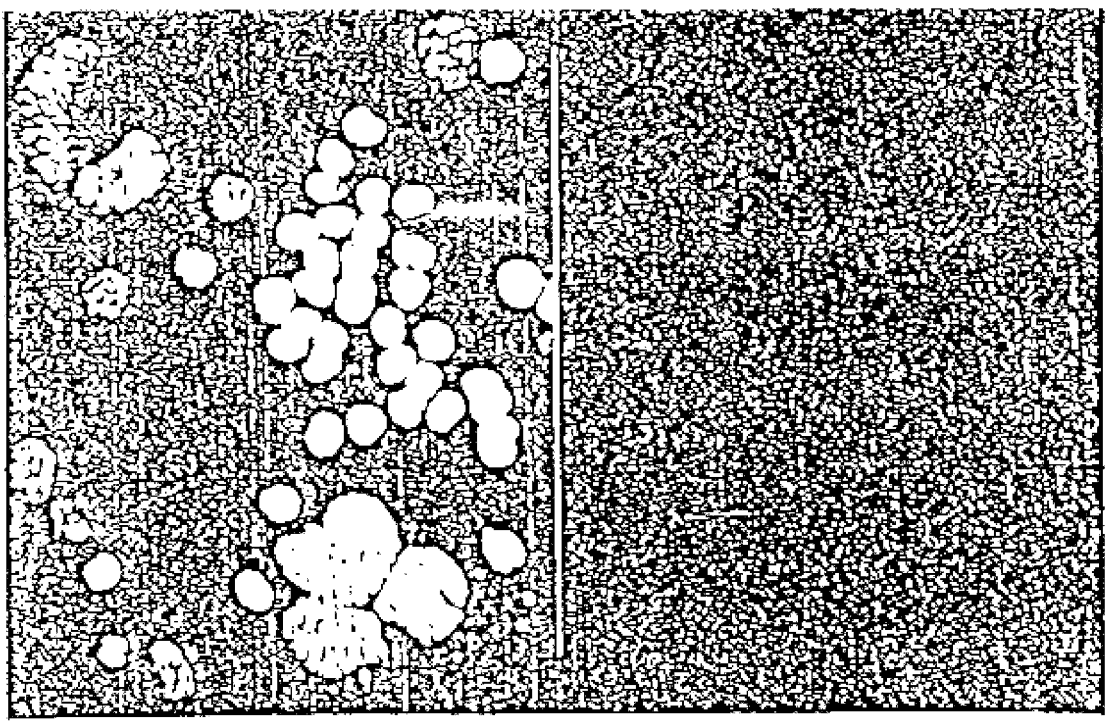
FIG. 8 is a photograph depicting 5-bromo-2deoxyuridine (BUdR) labeling of replicating nuclei in adherent 32D-EGFR cells.

To distinguish between these two possibilities, 5-bromo-2'deoxyuridine (BUdR) was added to nine day old and twenty-one day old cocultures and allowed to incorporate into relicating DNA for various lengths of time. To visualize and quantiate cells that had undergone DNA replication during the time of exposure to BUdR, monolayers containing adherent 32D-EGFR cells and supernatants containing non-adherent cells were fixed and stained for indirect immunofluorescence with anti-BUdR antibody and rhodamine-conjugated secondary antibody. The stromal cells were essentially quiescent with fewer than 0.5% of the nuclei becoming labeled under any of the conditions tested (FIG. 8 and Table 2). A significant proportion of adherent 32D-EGFR cells incorporated BUdR into the nucleus (FIG. 8 and Table 2). In nine day old cocultures, this proportion increased progressively with time of exposure to BUdR, reaching 38% of the adherent cells after a twenty-four hour exposure to BUdR. In twenty-one day old cocultures, as many as 30% of the cells became labeled after only three hours of exposure to BUdR, but this proportion increased slowly with extended labeling times (Table 2). In contrast to the high labeling index observed in adherent cells, only 10% or fewer of the non-adherent cells recovered from the cocultures became labeled (Table 2). This number included any cells that detached from the monolayers during collection of the media at the end of the labeling period. Furthermore, removal of the non-adherent cells from the cultures before a short (three hours) labeling of the cell layers with BUdR had essentially no effect on the proportion of adherent 32D-EGFR cells containing labeled nuclei (Table 2). From these results, it was concluded that 32D-

EGFR cells replicated their DNA while they were bound to membrane proTGF-α on the stromal cell monolayer.

TABLE 2

DNA replication in adherent and non-adherent 32D-EGFR cells

| Coculture age (days) | Exposure to BUdR (hours) | % of labeled nuclei[a] Adherent cells | Non-adherent cells |
|---|---|---|---|
| 9 | 3 | 8 | NT[c] |
|   | 9 | 21 | 7 |
|   | 12 | 25 | 8 |
|   | 24 | 38 | 6 |
| 21 | 3 | 30 | 11 |
|   | 3[b] | 29 | — |
|   | 12 | 37 | NT |
|   | 24 | 48 | NT |

[a]Number of rhodamine-labeled nuclei/number of bisbenzimide-labeled nuclei × 100 300–400 nuclei were scored per experimental condition.
[b]The culture medium containing non-adherent cells was removed before labeling the adherent cell layers with BUdR.
[c]NT, not tested.

EXAMPLE 2

Recovery of Donor Origin Stromal (GPTGFα) and Hematopietic (32DEGFR) Cells from Transplanted Mice The presence of donor origin stromal cells were detected by plating fresh bone marrow from control and transplanted mice (9 weeks after transplant with GPTGFα cells and 1 week after a second transplant of 32D-EGF-R cells) at $5 \times 10^5$ cells/60 mm dish and selecting with 300 μg/ml of G418. Results are shown in Table 3 as the mean-SD of 3 plates/hind limb from each of the three to five mice per group.

The presence and homing of the donor origin 32D-EGF-R cells was detected by plating fresh bone marrow cells from control and transplanted mice at $5 \times 10^6$ cells/60 mm dish and selecting with 25 μg/ml mycophenolic acid and 30 ng/ml EGF-R. Binding of $^{125}$I-labelled EGF was assayed. Equivalent numbers of cells were washed and incubated with $^{125}$I-labelled EGF. The extent of nonspecific binding was measured by incubating cells in the presence of a 100-fold excess of unlabelled EGF and these values were subtracted from bound counts. The results are set forth in Table 3. The data are mean=SD of triplicate determinations/hind limb from each of three to five mice/group. Other controls were FBM from C57BL/6 mice (1.5=0.86 cpm/$10^5$ cells) 32D cl 3 cells (<0.1 cpm/$10^5$ cells) and 32D-EGF-R cells (171.4= 12.5 cpm/10 cells).

The data indicates that C57BL/6J mice are stably engrafted in vivo with a clonal stromal cell line producing recombinant TGFα (G?-TGFα) to provide an in vivo microenvironment to which 32D-EGFR cells will home. As shown in Table 3, mice prepared for high dose irradiation of both hind limbs and a total body irradiation dose which was sublethal were engrafted in vivo by intravenous injection of the GP-TGFα cell line. Six months later, the animals received a total body irradiation dose and injection intravenously, of 32D-EGFR cells. Donor origin stromal cells were then measured several weeks later by explant of adherent cells showing neo$^r$ resistance (a selection marker linked to the TGFα construct) and hematopoietic cells showing mycoprhenolic acid resistance (a resistance gene linked to the EGFR construct). The controls included animals irradiated and injected with the stromal cell line only, and other animals irradiated and injected with the TGFα producing stromal cell line and then with the 32D cell line that did not have the EGFR receptor. The results showed that only in combination of GP-TGFα cell line engrafted, and then 32D EGFR inoculation, was there evidence for survival of 32D-EGFR cells in vivo. Furthermore, these cells were only detected at sites of stable engraftment of GP-TGFα stromal cells. Mice not injected with the stromal cell line, but inoculated with 32-EGFR cells, showed no detectable hematopoiotic cells at the same time interval. Thus, the data provide in vivo evidence for the engraftment of stromal cell lines followed by homing of hematopoietic stem cell lines using the receptor ligand interaction as the mechanism for homing of hematopoietic to the stromal cells in vivo.

TABLE 3

TOTAL NUMBER (% RESISTANT)*

| MICE | STROMAL CELLS G418[I] CFU-F/LIMB | HEMATOPOIETIC CELLS Cells/limb Mycophenolic acid × $10^5$ | $_I125_I$-EGF bound cpm/$10^5$ cells |
|---|---|---|---|
| Control –GPTCFα +32DEGFR | RHL 2.0 ± 1.9 (3.0 ± 2.9%) LHL 0 (0) | 0.8 ± 0.45 (2.2 ± 1.2%) 1.3 ± 0.96 (3.6 ± 2.6%) | 0.7 ± 0.1 N.T. |
| TRANS-PLANTED +GPTGFα +32DECFR | RHL 11.3 ± 1.7** (17.3 ± 2.6% LHL 11.0 ± 3.0** (16.9 ± 4.6%) | 9.2 ± 3.4 (30 ± 11%) 15.2 ± 8.0 (51 ± 26%) | 4.7 ± 0.16 N.T. |

*% resistant cells: number of cells recovered in presence of drug/number of cells in absence of drug × 100
**p < 0.05 compared to control mice.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method for homing hematopoietic stem cells to transplanted bone marrow stromal cells and inducing proliferation of those stem cells in a host, comprising
   administering to the host stromal cells genetically engineered to express a first member of a ligand-receptor binding pair; and subsequently
   administering to the host hematopoietic stem cells genetically engineered to express a second member of said ligand-receptor binding pair, whereby binding of said first member to said second member homes said stem cells to said stromal cells and induces proliferation of said stem cells.

2. The method of claim 1, wherein either said genetically engineered stromal cells or said genetically engineered hematopoietic stem cells are produced by transfecting said cells with a retroviral vector that encodes a member of said ligand-receptor binding pair.

3. A method according to claim 1 wherein the ligand-receptor binding pair is selected from the group consisting of transforming growth factor and transforming growth factor receptor or epidermal growth factor receptor; epidermal growth factor and epidermal growth factor receptor; tumor necrosis factor-α and tumor necrosis factor-receptor; interferon and interferon receptor; platelet derived growth factor and platelet derived growth factor receptor; transferrin and transferrin receptor; avidin and biotin or antibiotin; antibody and antigen pairs; interleukin and interleukin receptor; granulocyte-macrophage colony stimulating factor and granulocyte-macrophage colony stimulating factor receptor; macrophage colony stimulating factor and macrophage colony stimulating factor receptor; granulocyte colony stimulating factor and granulocyte colony stimulating factor receptor; and sugar molecules and sugar receptors.

4. A method according to claim 1 wherein the hematopoietic stem cells are 32D or a non-adherent stem cell derived from a human long term bone marrow culture.

5. A method according to claim 1 wherein the bone marrow stromal cells are selected from the group consisting of GBL/6, KM101, KM102, KM103, KM104 and KM105.

6. A method according to claim 1 wherein the stromal cells are capable of expressing a recombinant ligand.

7. A method according to claim 6 wherein the ligand is pro-transforming growth factor-α.

8. A method according to claim 1 wherein the hematopoietic stem cells are capable of expressing a recombinant receptor.

9. A method according to claim 8 wherein the receptor is an epidermal growth factor receptor.

* * * * *